US00PP09511P

United States Patent [19]

Tanikoshi et al.

[11] Patent Number: Plant 9,511

[45] Date of Patent: Apr. 16, 1996

[54] HOPS NAMED 'FURANO NO. 18'

[75] Inventors: Tokio Tanikoshi, Hokkaido; Yasunori Arai, Kokubun-ji; Yutaka Itoga, Hokkaido; Masanobu Goto, Hokkaido; Narushi Suda, Hokkaido, all of Japan

[73] Assignee: Sapporo Breweries Limited, Tokyo, Japan

[21] Appl. No.: 271,501

[22] Filed: Jul. 7, 1994

[51] Int. Cl.[6] ..... A01H 5/00

[52] U.S. Cl. ..... Plt./100

[58] Field of Search ..... Plt./100

[56] References Cited

U.S. PATENT DOCUMENTS

P.P. 8,823 7/1994 Probasco ..... Plt./100

OTHER PUBLICATIONS

Mori, Yoshitada, Development of New Hop Varieties (Furano Ace and Sorachi Ace) of Aroma–Type Hop in Japan, Sapporo Breweries Ltd., Mar., 1988.

Mori, Yoshitada, A Review and Future Prospect of Hop Breeding in Japan—Development of New Hop Varieties at Sapporo Breweries Ltd., vol. 27, 1981, Bulletin of Brewing Science, pp. 23–43.

*Primary Examiner*—James R. Feyrer

*Attorney, Agent, or Firm*—Oblon, Spivak, McClelland, Maier & Neustadt

[57] ABSTRACT

A new and distinct variety of Hops, named Hokuto-Ace, is described, which matures rapidly, has excellent bitterness and aroma, and exhibits increased disease resistance, particularly toward downy mildew and gray mold.

4 Drawing Sheets

BACKGROUND OF THE NEW PLANT

The present invention relates to a new and distinct variety of hops which matures rapidly, has excellent bitterness and aroma, and exhibits increased disease resistance, particularly toward downy mildew and gray mold.

The variety is further characterized by being of relatively low height, having a reddish-purple crista color, and a main vine which is reddish-green. The cones are greenish-yellow and change to pale green as they mature. The cone shape is elongated spheroid and large. The plant, which is plagiotropic, has a very high content of humulone and farnesene and a very low content of cohumulone.

The new plant originated from a cross-breeding in 1983 of the mother, Sorachi-ace, and father, seedling of Saaz from open pollination, at Hokkaido Center, Plant Bioengineering Research Laboratories, Sapporo Breweries, Ltd. Due to the hybrid character of this plant, its unique and valuable characteristics can be assured to be retained only through asexual or vegetative propagation.

DETAILED BOTANICAL DESCRIPTION OF THE PLANT

Figure 1:
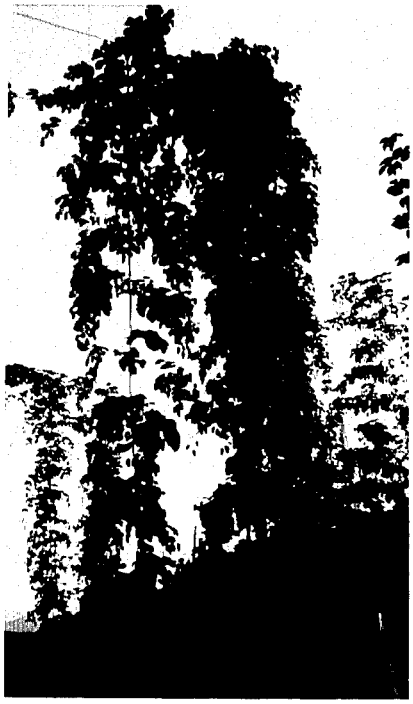
FIG. 1 is a complete view of the new variety, Hokuto-Ace.
Figure 2:
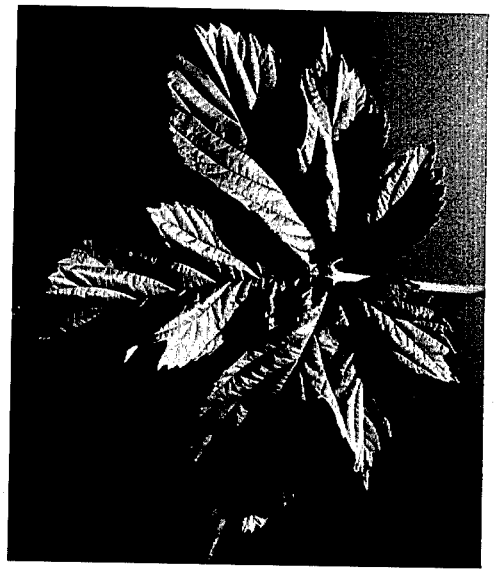
FIG. 2 is a top view of a mature leaf of Hokuto-Ace.
Figure 3:
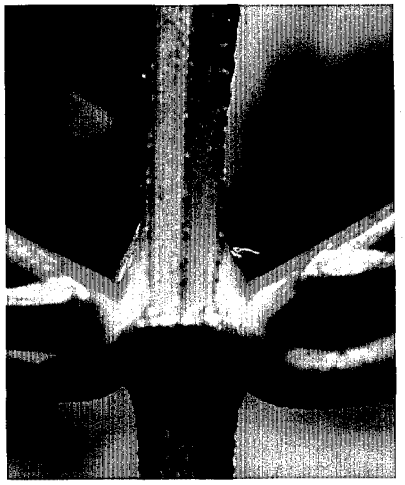
FIG. 3 is a side view of a main vine of Hokuto-Ace.
Figure 4:
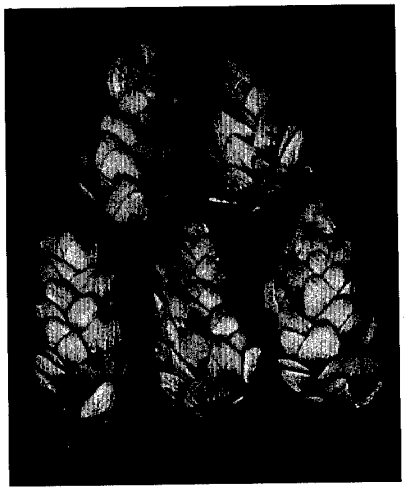
FIG. 4 is a side view of five mature cones of Hokuto-Ace.

Sorachi-Ace is a proprietary variety developed by Sapporo (registration pursuant to the Seed and Seedling law applied for in 1983, registered as a variety in 1984). Saaz is a general term used to refer to a group of hop varieties originating in Czechoslovakia, which includes several varieties derived from Oswald Clone No. 3,172,114. It is not known which specific Saaz varieties were the parents of the Saaz seedling which is the pollen parent of Furano No. 18.

The following is a detailed description of the characteristics of the new variety as observed at the same Research Laboratory noted above. Color designations are made by reference to J.H.S. Color Chart (Japan Horticultural Scale) and R.H.S. Colour Chart (Royal Horticultural Society), except where common terms of color definition are employed.

The new variety was propagated and is maintained at Sapporo Breweries, Ltd., Hokkaido, Sorachi-gun, Kami-furanomachi Higashi Line 4 Number 25, Japan. The multiplication of the plant was performed by separating roots from existing stock and then cultivating and propagating at the test field.

The hops plant, "Furano No. 18", has been found to be stable and the clonal progeny of this plant have been found to be identical to the original selection in all distinguishing characteristics.

The following represents a breeding history.

1983 Artificial crossing

1984 F1 breeding, selecting downy mildew resistant individuals

1985 Selecting individuals, sexing, selecting downy mildew resistant and gray mold resistant individuals

1986

Preliminary test for yield

Preliminary test for quality assessment

1987 Yield test, quality assessment test

1988 Fertility assessment test, quality assessment test

1989 Fertility assessment test, quality assessment test

1990 Selection based on alpha acid composition

1991 Selection based on essential oil composition

The finally selected plant was initially denominated "Sapporo No. 1", but has more recently been renamed "Furano No. 18", by which it will be internationally known.

The process of selection was as follows:

| No. individuals tested | No. individuals selected |
|---|---|
| 1983 Cross breeding | 1345 F1 seeds obtained |

-continued

| No. individuals tested | No. individuals selected |
|---|---|
| 1984 1345 seeds (1089 germinated) | 143 individuals selected |
| 1984 143 individuals | 46 individuals selected |
| 1986 46 individuals | 11 individuals selected |
| 1987 11 individuals | 8 individuals selected |
| 1988 8 individuals | 8 individuals selected |
| 1989 5 individuals | 3 individuals selected |
| 1990 2 individuals | 2 individuals selected |
| 1991 2 individuals | 1 individual selected |
| 1992 1 individuals | 1 individuals selected |

The novel plant of this invention was under final test and observation for two and one-half years; a period from April 1990 to September 1992, at which time the selection had been multiplied to a population sufficient to occupy five acres.

The plant of this invention is an early ripening variety-mesophytic type, suited for cultivation in Hokkaido and the northern area of Tohoku, and is suitable for large scale mechanical picking. Growths are medium in thickness and the height is low. It is resistant against downy mildew and gray mold, is easy to cultivate and has an excellent quality as it contains very little cohumulone, which includes α-acids, a main component of bitterness, but much humulone and farnesene.

The new variety is particularly suitable for growing in Hokkaido, the northern part of Tohoku. This variety is also advantageous as it requires no excessive growth control as is the case with Shinshu-wase, the predominant species. The new variety also requires no lowering of vines or picking of primary side branches.

The morphological characteristics of the new variety are described hereinbelow, and are summarized in Table 1 following thereafter.

The general growth form of the new variety is clavate, with the mature plant being of medium height. The color of the young shoots is (ISCC-NBS) reddish-purple with the angle of the shoot to the ground being squint. The main vine is (ISCC-NBS) reddish-green in color with the crista color being (ISCC-NBS) reddish purple.

As used herein, the term "squint" denotes a range of angles of the stem to soil of between 30° and 70°. The term "creeping" refers to a range of angles of from 0° to 30°, and the term "straight" refers to a range of angles between 70° and 90°. The term "crista" denotes the line connecting the six angles on a cross-section of the hexagonal stem of the plant.

The degree of twining of the main vine is medium with a glabrate degree of node hair. The length of the internode is medium with a medium number of nodes.

The length of the internode provided is for the internode at approximately 1.5 m. from the ground for a vine which has reached a height of 2.75 m. An internode of under 30 cm. is "short"; from 30–40 cm. is "medium"; and 40 cm. or more is "long". The internode of Furano No. 18 averages 35 cm., with the range being from 29–49 cm., and is therefor of "medium" length.

The lateral branching of the new variety is medium in length with a medium degree of branching. The location of inflorescence is at the tertiary branch with the density of inflorescence being medium to dense. The storm resistance of the lateral branching is medium to strong.

The increased extent of lateral branching of Furano No. 18 appears to be an inherent feature of the plant. Shinshu-wase, by comparison requires bending of the stem so that the vine will grow laterally and/or clipping of the upper stem in order to stop vertical growth and promote lateral growth, so that the cones on the branches below will be exposed to sunlight. Due to the typically excessive growth at the top portion of the vines of Shinshu-wase, the cones below are shaded. Because of the increased external lateral branching in Furano No. 18, the foregoing measures are not necessary to expose the lower cones to sunlight.

As used herein, the word "medium" when used to describe the length of lateral branching denotes a length of between 60 and 140 cm. The average length or lateral branching of the present plant is 135 cm., with a range of between 110 to 165 cm. Thus, it is "medium" in length. The term 37 short" is used to denote the range of lengths up to 60 cm., and "long" denotes a range of from 140 cm. and over. The "degree of branching" is estimated by visual observation as is the "density of inflorescence".

The leaves are (ISCC–NBS) light-green in color when young, and remain so when mature. The leaves have a palmate blade form with seven lobes. The sinus cleft has a medium depth and the marginal serrations are of a serrated form. The form of the blade base is close.

The color of the young leaves and the mature leaves is "dark yellow-green" which is 3508 on the B.H.S./J.H.S. Color Chart.

The cones are yellowish-green (ISCC-NBS) in color and are of an elongated spheroid form. They are large in size. The number of blacts and blacteroles is medium and the cone weight is also medium. The number of cones per vine and the weight ratio of cones to foliage and vine may each be characterized as medium.

The blacts are (ISCC-NBS) yellowish-green in color and are of an oval form. The tip form is acute with a medium length. The length to width ratio is medium.

The blacteroles are of a (ISCC-NBS) yellowish-green color and are ovate to ellipsoid in form. They are medium in length with a medium length to width ratio.

The strigs are of medium thickness with a medium density of flowers. The lupulin is (ISCC-NBS) yellow in color and medium in size. The lupulin blacteroles are medium to abundant in number.

The new variety exhibits a mid-stage of flowering, with cone production also occurring at mid-stage. Ripening also occurs at mid-stage.

The new variety is, as noted above, disease-resistant and is, in particular, resistant to downy mildew. In more detail, the stem is resistant, the leaf is mildly resistant and the cone is resistant. The new variety is also stunt disease resistant.

The new variety has a resin content such that a medium content of resins may be noted. It has a medium content of α-acids with a medium to high β-fraction. The new variety has a medium content of hard resins with a high ratio of β-fraction to α-acids. The stragebility of α-acids is medium.

The α-acid constituents may be described as follows. The humulone content is very high, while the cohumulone content and adhumulone content are each low. The new variety, thus, has excellent bitterness.

The new variety also exhibits a medium degree of aroma, with a medium content of essential oils.

TABLE 1

| Item | Categories Observed | |
|---|---|---|
| Number | Item | Classification |
| | MORPHOLOGICAL CHARACTERISTICS | |
| I-1 | General Growth Form | 2 = fusiform, 4 = columnar, 6 = clavate, 8 = capitate<br>2 4 ⑥ 8 |
| I-2 | Height | 3 = low, 5 = medium, 7 = high<br>3 ⑤ 7 |
| I-3 | Young Shoots | |
| I-3-1 | Color | 2 = yellow, 3 = yellowish green, |

TABLE 1-continued

| | | |
|---|---|---|
| | | 4 = green, 5 = reddish green, 6 = red, 7 = reddish purple, 8 = purple<br>2 3 4 5 6 ⑦ 8 |
| I-3-2 | Angle of Shoot to Ground | 3 = creeping, 5 = squint, 7 = straight<br>3 ⑤ 7 |
| I-4 | Main Vine | |
| I-4-1 | Color | (legend same as I-3-1)<br>2 3 4 ⑤ 6 7 8 |
| I-4-2 | Color of Crista | (legend same as I-3-1)<br>2 3 4 5 6 ⑦ 8 |
| I-4-3 | Degree of Twining | 3 = weak, 5 = medium, 7 = strong<br>3 ⑤ 7 |
| I-4-4 | Degree of Hair of Node | 1 = glabrate, 2 = very few 3 = few, 4 = few to medium, 5 = medium, 6 = medium to abundant, 7 = abundant, 8 = very abundant<br>① 2 3 4 5 6 7 8 |
| I-4-5 | Length of Internode | 3 = short, 5 = medium, 7 = long<br>3 ⑤ 7 |
| I-4-6 | Number of Nodes | 3 = few, 5 = medium, 7 = abundant<br>3 ⑤ 7 |
| I-5 | Lateral Branch | |
| I-5-1 | Length | 3 = short, 5 = medium, 7 = long<br>3 ⑤ 7 |
| I-5-2 | Degree of Branching | 3 = few, 5 = medium, 7 = many<br>3 ⑤ 7 |
| I-5-3 | Location of Inflorescence | 3 = main vine, 4 = priamry branch, 5 = secondary branch, 6 = tertiary branch, 7 = >fourth branch<br>3 4 5 ⑥ 7 |
| I-5-4 | Density of Inflorescence | 2 = very sparse, 3 = sparse, 4 = sparse to medium, 5 = medium, 6 = medium to dense, 7 = dense, 8 = very dense<br>2 3 4 5 ⑥ 7 8 |
| I-5-5 | Storm Resistance | 2 = very weak, 3 = weak, 4 = weak to medium, 5 = medium, 6 = medium to strong, 7 = strong, 8 = very strong<br>2 3 4 5 ⑥ 7 8 |
| I-6 | Leaves | |
| I-6-1 | Color | |
| I-6-1-1 | Young Leaves | 3 = yellow, 4 = pale yellow green, 5 = light green, 6 = green, 7 = vivid green, 8 = deep green<br>3 4 ⑤ 6 7 8 |
| I-6-1-2 | Mature Leaves | (legend same as 1-6-1-1)<br>3 4 ⑤ 6 7 8 |
| I-6-2 | Form | |
| I-6-2-1 | Blade Form | 3 = cordate, 5 = medium, 7 = palmate<br>3 5 ⑦ |
| I-6-2-2 | Number of Lobes | 1 = 0, 3 = 3, 5 = 5, 7 = 7, 9 = 8<<br>1 3 5 ⑦ 9 |
| I-6-2-3 | Depth of Sinus Cleft | 3 = shallow, 4 = shallow to medium, 5 = medium, 6 = medium to deep, 7 = deep<br>3 4 ⑤ 6 7 |
| I-6-2-4 | Form of Marginal Serrations | 3 = denate, 5 = medium, 7 = serrate<br>3 5 ⑦ |
| I-6-2-5 | Form of Blade Base | 3 = open, 5 = medium, 7 = close<br>3 5 ⑦ |
| I-6-3 | Size | |
| I-6-3-1 | Length of Blade | 3 = short, 5 = medium, 7 = long<br>3 ⑤ 7 |
| I-6-3-2 | Length Ratio of Blade to Petiole | 3 = low, 5 = medium, 7 = high<br>3 ⑤ 7 |

TABLE 1-continued

| | | |
|---|---|---|
| I-7 | Cones | |
| I-7-1 | Color | 3 = greenish yellow, 4 = yellowish green, 5 = green, 6 = vivid green, 7 = deep green<br>3 ④ 5 6 7 |
| I-7-2 | Form | 2 = round, 3 = ovate, 4 = oval, 5 = elongated spheroid, 6 = elongated ovate, 7 = oblong<br>2 3 4 ⑤ 6 7 |
| I-7-3 | Size | 2 = very small, 3 = small, 4 = small to medium, 5 = medium, 6 = medium to large, 7 = large, 8 = very large<br>2 3 4 5 6 ⑦ 8 |
| I-7-4 | Number of Blacts and Blacteoles | 3 = few, 5 = medium, 7 = many<br>3 ⑤ 7 |
| I-7-5 | 100 Cone Weight | 3 = light, 5 = medium, 7 = heavy<br>3 ⑤ 7 |
| I-7-6 | Number of Cones per Vine | 3 = few, 5 = medium, 7 = many<br>3 ⑤ 7 |
| I-7-7 | Weight Ratio of Cones to Foliage and Vine | 3 = low, 5 = medium, 7 = high<br>3 ⑤ 7 |
| I-8 | Blacts | |
| I-8-1 | Color | 3 = greenish yellow, 4 = yellowish green, 5 = green, 6 = vivid green, 7 = deep green<br>3 ④ 5 6 7 |
| I-8-2 | Form | 3 = oblate, 4 = cordate, 5 = oval, 6 = obovate, 7 = ellipsoid, 8 = lancelate<br>3 4 ⑤ 6 7 8 |
| I-8-3 | Form of Tips | 3 = acute, 5 = subacutely, 7 = acuminate<br>③ 5 7 |
| I-8-4 | Length | 3 = short, 5 = medium, 7 = long<br>3 ⑤ 7 |
| I-8-5 | Length to Width Ratio | 3 = low, 5 = medium, 7 = high<br>3 ⑤ 7 |
| I-9 | Blacteoles | |
| I-9-1 | Color | 3 = greenish yellow, 4 = yellowish green, 5 = green, 6 = vivid green, 7 = deep green<br>3 ④ 5 6 7 |
| I-9-2 | Form | 3 = ovate, 4 = ovate to ellipsoid, 5 = ellipsoid, 6 = oblong<br>3 ④ 5 6 |
| I-9-3 | Length | 3 = short, 5 = medium, 7 = long<br>3 ⑤ 7 |
| I-9-4 | Length to Width Ratio | 3 = low, 5 = medium, 7 = high<br>3 ⑤ 7 |
| I-10 | Strigs | |
| I-10-1 | Thickness | 2 = very thin, 3 = thin, 4 = thin to medium, 5 = medium, 6 = medium to thin, 7 = thick, 8 = very thick<br>2 3 4 ⑤ 6 7 8 |
| I-10-2 | Density of Flowers | 3 = sparse, 4 = sparse to medium, 5 = medium, 6 = medium to dense, 7 = dense<br>3 4 ⑤ 6 7 |
| I-11 | Lupulin | |
| I-11-1 | Color | 3 = pale yellow, 5 = yellow, 7 = orange<br>3 ⑤ 7 |
| I-11-2 | Size | 3 = small, 4 = small to medium, 5 = medium, 6 = medium to large, 7 = large<br>3 4 ⑤ 6 7 |
| I-11-13 | Blacteoles | 2 = very few, 3 = few, 4 = few to medium, 5 = medium, 6 = medium to abundant, 7 = abundant, 8 = very abundant<br>2 3 4 5 ⑥ 7 8 |

TABLE 1-continued

| Item Number | Categories Observed: Cultivation Site Control Species (for reference) Shinshu-wase | Furano-ace | Sorachi-ace |
|---|---|---|---|
| | MORPHOLOGICAL CHARACTERISTICS | | |
| I-1 | 8 | 6 | 4 |
| I-2 | 7 | 3 | 3 |
| I-3 | | | |
| I-3-1 | 7 | 7 | 7 |
| I-3-2 | 5 | 5 | 5 |
| I-4 | | | |
| I-4-1 | 5 | 5 | 4 |
| I-4-2 | 7 | 6 | 5 |
| I-4-3 | 5 | 5 | 5 |
| I-4-4 | 5 | 1 | 1 |
| I-4-5 | 5 | 5 | 5 |
| I-4-6 | 5 | 5 | 5 |
| I-5 | | | |
| I-5-1 | 5 | 5 | 5 |
| I-5-2 | 5 | 5 | 5 |
| I-5-3 | 6 | 6 | 6 |
| I-5-4 | 6 | 5 | 4 |
| I-5-5 | 5 | 5 | 6 |
| I-6 | | | |
| I-6-1 | | | |
| I-6-1-1 | 5 | 5 | 5 |
| I-6-1-2 | 5 | 6 | 6 |
| I-6-2 | | | |
| I-6-2-1 | 7 | 7 | 7 |
| I-6-2-2 | 5 | 5 | 5 |
| I-6-2-3 | 6 | 5 | 5 |
| I-6-2-4 | 7 | 7 | 7 |
| I-6-2-5 | 5 | 5 | 7 |
| I-6-3 | | | |
| I-6-3-1 | 5 | 5 | 3 |
| I-6-3-2 | 5 | 5 | 5 |
| I-7 | | | |
| I-7-1 | 4 | 5 | 5 |
| I-7-2 | 5 | 5 | 4 |
| I-7-3 | 5 | 5 | 5 |
| I-7-4 | 5 | 5 | 3 |
| I-7-5 | 5 | 5 | 5 |
| I-7-6 | 5 | 3 | 5 |
| I-7-7 | 5 | 5 | 5 |
| I-8 | | | |
| I-8-1 | 4 | 5 | 5 |
| I-8-2 | 5 | 7 | 5 |
| I-8-3 | 3 | 3 | 5 |
| I-8-4 | 5 | 7 | 5 |
| I-8-5 | 5 | 3 | 3 |
| I-9 | | | |
| I-9-1 | 4 | 5 | 5 |
| I-9-2 | 4 | 5 | 3 |
| I-9-3 | 5 | 5 | 5 |
| I-9-4 | 5 | 5 | 3 |
| I-10 | | | |
| I-10-1 | 5 | 6 | 5 |
| I-10-2 | 5 | 6 | 6 |
| I-11 | | | |
| I-11-1 | 5 | 5 | 5 |
| I-11-2 | 5 | 5 | 6 |
| I-11-13 | 5 | 5 | 6 |

| Item Number | Categories Observed: Item | Classification |
|---|---|---|
| | ECOLOGICAL CHARACTERISTICS | |
| II-1 | Maturity | |
| II-1-1 | Stage of Flowering | 3 = very early, 4 = early, 5 = mid, 6 = late, 7 = very late<br>3 4 ⑤ 6 7 |
| II-1-2 | Stage of Producing Cones | 3 = very early, 4 = early, 5 = mid, 6 = late, 7 = very late<br>3 4 ⑤ 6 7 |
| II-1-3 | Ripening | 3 = very early, 4 = early, 5 = mid, 6 = late, 7 = very late<br>3 4 ⑤ 6 7 |
| II-2 | Disease Resistance | |
| II-2-1 | Downy Mildew | |
| II-2-1-1 | Stem | 3 = susceptlible, 4 = mildly susceptible, 5 = moderate, 6 = midly resistant, 7 = resistant<br>3 4 5 6 ⑦ |
| II-2-1-2 | Leaf | 3 = susceptible, 4 = mildly susceptible, 5 = moderate, 6 = mildly resitant, 7 = resistant<br>3 4 5 ⑥ 7 |
| II-2-1-3 | Cone | 3 = susceptible, 4 = mildly susceptible, 5 = moderate, 6 = mildly resitant, 7 = resistant<br>3 4 5 6 ⑦ |
| II-2-2 | Stunt Disease | 3 = susceptible, 4 = mildly susceptible, 5 = moderate, 6 = mildly resistant, 7 = resistant<br>3 4 5 6 7 |
| II-3 | Insect Resistance | |
| II-4 | Content of Resins | |
| II-4-1 | Total Resins | 3 = low, 5 = medium, 7 = high, 9 = very high<br>3 ⑤ 7 9 |
| II-4-2 | α Acids | 4 = low, 5 = medium, 6 = medium to high, 7 = high, 8 = very high<br>4 ⑤ 6 7 8 |
| II-4-3 | β Fraction | 4 = low, 5 = medium, 6 = medium to high, 7 = high, 8 = very high<br>4 5 ⑥ 7 8 |
| II-4-4 | Hard Resins | 3 = low, 5 = medium, 7 = high<br>3 ⑤ 7 |
| II-4-5 | Ratio of β Fraction to α Acids | 3 = low, 5 = medium, 7 = high<br>3 5 ⑦ |
| II-4-6 | Stragebility of α Acids | 3 = bad, 5 = medium, 7 = good<br>3 ⑤ 7 |
| II-4-7 | Constituents of α Acids | |
| II-4-7-1 | Humulone | 3 = low, 5 = medium, 7 = high, 9 = very high<br>3 5 7 ⑨ |
| II-4-7-2 | Cohumulone | 3 = low, 5 = medium, 7 = high<br>③ 5 7 |
| II-4-7-3 | Adhumulone | 3 = low, 5 = medium, 7 = high<br>③ 5 7 |
| II-5 | Degree of Aroma | |
| II-5-1 | Degree of Aroma | 3 = mild, 4 = mild to medium, 5 = medium, 6 = medium to heavy, 7 = heavy<br>3 4 ⑤ 6 7 |
| II-5-2 | Content of Essential Oils | 3 = low, 5 = medium, 7 = high<br>3 ⑤ 7 |

| Item Number | Categories Observed: Cultivation Site Control Species (for reference) Shinshu-wase | Furano-ace | Sorachi-ace |
|---|---|---|---|
| | ECOLOGICAL CHARACTERISTICS | | |
| II-1 | | | |
| II-1-1 | 6 | 4 | 5 |
| II-1-2 | 6 | 4 | 6 |
| II-1-3 | 6 | 5 | 5 |
| II-2 | | | |
| II-2-1 | | | |
| II-2-1-1 | 5 | 7 | 7 |
| II-2-1-2 | 5 | 6 | 6 |

TABLE 1-continued

| | | | |
|---|---|---|---|
| II-2-1-3 | 5 | 7 | 7 |
| II-2-2 | 5 | — | — |
| II-3 | | | |
| II-4 | | | |
| II-4-1 | 5 | 5 | 7 |
| II-4-2 | 5 | 5 | 8 |
| II-4-3 | 5 | 5 | 5 |
| II-4-4 | 5 | 5 | 5 |
| II-4-5 | 5 | 5 | 3 |
| II-4-6 | 5 | 5 | 5 |
| II-4-7 | | | |
| II-4-7-1 | 5 | 9 | 9 |
| II-4-7-2 | 7 | 3 | 3 |
| II-4-7-3 | 3 | 3 | 3 |
| II-5-1 | 5 | 5 | 5 |
| II-5-2 | 5 | 5 | 5 |

In Table 2 hereinbelow are represented trial data generated for years 1990, 1991 and 1992.

This Table features a comparison from among the new variety and three comparison species: Shinshu-wase, Furano-ace and Sorachi-ace.

TABLE 2

A. Growth Characteristics

| Survey Items | Year of Survey | Applied-for Species (Sappro #1) |
|---|---|---|
| Young Shoots | '90 | May 1 |
| | '91 | April 30 |
| | '92 | May 11 |
| Second Stage | '90 | June 22 |
| | '91 | June 14 |
| | '92 | June 23 |
| Efforescence | 90 | July 10 |
| | '91 | July 13 |
| | '92 | July 15 |
| Fruit Formation | '90 | July 18 |
| | '91 | July 31 |
| | '92 | July 25 |
| Maturation | '90 | August 21 |
| | '91 | August 26 |
| | '92 | August 24 |
| Foliage | '90 | medium |
| | '91 | medium dense |
| | '92 | medium dense |
| Weight Gain (kg/10a) | '90 | 140 |
| | '91 | 181 |
| | '92 | 185 |
| DISEASE RESISTANCE | | |
| Downy Mildew | '90 | Strong |
| | '91 | Strong |
| | '92 | Strong |
| Gray Mold | '90 | med. to strong |
| | '91 | med to strong |
| | '92 | med. to strong |

| Survey Items | Comparison Species | | |
|---|---|---|---|
| | Shinshu-wase | Furano-ace | Sorachi-ace |
| Young Shoots | April 30 | April 30 | April 30 |
| | April 28 | April 26 | April 27 |
| | May 7 | May 6 | May 6 |
| Second Stage | June 26 | 26 | June 22 |
| | June 13 | 15 | June 14 |
| | June 20 | 22 | June 20 |
| Efflorescence | July 15 | July 5 | July 12 |
| | July 23 | July 2 | July 10 |
| | July 23 | July 12 | July 15 |
| Fruit Formation | July 28 | July 16 | July 23 |
| | August 7 | July 20 | August 1 |
| Maturation | August 6 | July 26 | July 30 |
| | August 26 | August 16 | August 25 |
| | September 6 | August 18 | August 25 |
| | September 2 | August 26 | August 30 |
| Foliage | medium | medium | dense |
| | medium | medium | dense |
| | med. to dense | medium | dense |
| Weight Gain (kg/10a) | 130 | 144 | 153 |
| | 170 | 144 | 165 |
| | 197 | 164 | 203 |
| DISEASE RESISTANCE | | | |
| Downy Mildew | Average | Strong | Strong |
| | Average | Strong | Strong |
| | Average | Strong | Strong |
| Gray Mold | Average | med. to strong | med. to strong |
| | Average | med. to strong | med. to strong |
| | Average | med. to strong | med. to strong |

B. Quality Survey

| Survey Items | Year of Survey | Applied-for Species (Sappro #1) |
|---|---|---|
| α Acids (Dry %) | '90 | 6.9 |
| | '91 | 6.0 |
| | '92 | 6.8 |
| β Acids (Dry %) | '90 | 9.6 |
| | '91 | 9.7 |
| | '92 | 6.5 |
| α/β Comparison | '90 | 0.72 |
| | '91 | 0.62 |
| | '92 | 1.05 |
| αAcid COMPOSITION COMPARISON | | |
| Cohumulone (Wt. %) | '90 | 22 |
| | '91 | 21 |
| | '92 | 24 |
| Humulone (Wt. %) | '90 | 78 |
| | '91 | 79 |
| | '92 | 76 |
| ESSENTIAL OIL CONTENT | | |
| Humulene (Dry %) | '90 | 22.8 |
| | '91 | 24.1 |
| | '92 | 25.6 |
| Caryophyllene (Dry %) | '90 | 9.6 |
| | '91 | 10.2 |
| | '92 | 11.5 |
| Hum/Ca Ratio (Dry %) | '90 | 2.4 |
| | '91 | 2.4 |
| | '92 | 2.2 |
| Farnesene (Dry %) | '90 | 27.4 |
| | '91 | 15.8 |
| | '92 | 9.4 |
| Myrcen (Dry %) | '90 | 23.9 |
| | '91 | 11.4 |
| | '92 | 34.5 |
| Aroma | '90 | Good |
| | '91 | |
| | '92 | |

| Survey Items | Comparison Species | | |
|---|---|---|---|
| | Shinshu-wase | Furano-ace | Sorachi-ace |
| α Acids (Dry %) | 5.6 | 5.3 | 12.6 |
| | 6.9 | 4.7 | 12.2 |
| | 5.6 | 5.7 | 12.9 |

TABLE 2-continued

| | | | |
|---|---|---|---|
| β Acids (Dry %) | 5.4 | 7.7 | 7.9 |
| | 7.8 | 7.4 | 8.2 |
| | 6.2 | 7.7 | 7.4 |
| α/β Comparison | 1.04 | 0.69 | 1.59 |
| | 0.88 | 0.64 | 1.49 |
| | 0.92 | 0.74 | 1.74 |
| α ACID COMPOSITION COMPARISON | | | |
| Cohumulone | 48 | 25 | 25 |
| (Wt %) | 48 | 26 | 29 |
| | 47 | 24 | 28 |
| Humulone | 52 | 75 | 75 |
| (Wt. %) | 52 | 74 | 71 |
| | 53 | 76 | 72 |
| ESSENTIAL OIL CONTENT | | | |
| Humulene | 22.8 | 24.2 | 33.7 |
| (Dry %) | 17.7 | 18.6 | 27.4 |
| | 21.7 | 21.3 | 24.1 |
| Caryophyllene | 9.9 | 14.3 | 11.2 |
| (Dry %) | 9.1 | 9.4 | 9.7 |
| | 10.3 | 9.4 | 8.1 |
| Hum/Ca Ratio | 2.2 | 1.7 | 3.0 |
| (Dry %) | 2.0 | 2.0 | 2.8 |
| | 2.1 | 2.3 | 3.0 |
| Farnesene | 0.7 | 20.1 | 6.3 |
| (Dry %) | 0.7 | 20.1 | 6.3 |
| Nycren | 31.4 | 17.1 | 28.6 |
| (Dry %) | 30.3 | 20.9 | 34.4 |
| | 23.7 | 35.4 | 43.3 |
| Aroma | Average | Good | Good |

Following is a detailed description of additional botanical and analytical chemical characteristics of the new variety. These characteristics depend to some extent upon cultural practices and climatic conditions and can vary with location and season.

TABLE 3

A. Color Characteristics
Fall color characteristics are unknown because the leaves are totally removed and destroyed during the harvesting procedure. Using the J.H.S. color chart, the following color characteristics for FURANO NO. 18 have been determined:
Leaf upper surface: 3508 dark yellow green
Leaf lower surface: n/a
Bine background: 3507 dark yellow green
Bine stripe: 0406 bright red
Cone bracteole: 3505 bright yellow green
Cone bract: 3505 bright yellow green
Sidearm stem: n/a
Sidearm stripe: (if red) - n/a
Sidearm stripe: (if green) - n/a B. Analytical Data of Cones
% Alpha acids (bale)*: 6.0 to 6.9 (EBC spectro-photometric method)
% Beta acids (bale)*: 6.3 to 9.8 (EBC spectro-photometric method)
Alpha/beta ratio*: 0.95 to 1.65
Cohumulone (% of alpha acids): average 22.0
Colupulone (% of beta acids): average n/a
Storage characteristics*: average 44.0% transformation after 6 months at 20 degrees C.
Total oils (ml/100° g.)**: average 1.2
Humulene (% of total oils): average 24.2
Caryophyllene (% of total oils): avergae 10.4
Humulene/caryophyllene ratio: average 2.3
Farnesene (% of total oils): average 17.5
Myrcene (% of total oils): average 23.3
Lupulin (% of total cone weight)**: average not established C. Analytical Data of Lupulin
% Alpha acids: Average (not established)
% Beta acids: Average (not established)

*Analytical data for alpha and beta acids determinded on hops with 0.0% cone moisture.
**Analytical data determined on hops with approxiamtely 5% cone moisture.

The present new variety of hops may be advantageously used as a raw material in the production of beer.

What is claimed as new and is desired to be secured by Letters Patent of the United States is:

1. A new and distinct variety of hops plant, substantially as described and claimed herein.

* * * * *

UNITED STATES PATENT AND TRADEMARK OFFICE

CERTIFICATE OF CORRECTION

PATENT NO. : PP 9,511
DATED : April 16, 1996
INVENTOR(S) : Tokio Tanikoshi et al.

It is certified that error appears in the above-identified patent and that said Letters Patent is hereby corrected as shown below:

Column 4,
Line 10, "37 short" should read -- short --.

Column 5,
Line 37, "denate" should read -- dentate --.

Column 11,
Line 19, "22.8" should read -- 22.2 --.
Lines 27 and 28,

| | | | |
|---|---|---|---|
| "Farnesene | "0.7 | 20.1 | 6.3 |
| (Dry %) | 0.7 | 20.1 | 6.3" |

should read

| | | | |
|---|---|---|---|
| -- Farnesene | 0.5 | 11.9 | 4.7 |
| (Dry %) | 0.3 | 8.1 | 5.4 -- |

Line 29, "Nycren" should read -- Myrcen --.

Column 12,
Line 23, "avergae" should read -- average --.

Signed and Sealed this

Fifth Day of February, 2002

*Attest:*

*Attesting Officer*

JAMES E. ROGAN
*Director of the United States Patent and Trademark Office*